(12) United States Patent
Newstadt et al.

(10) Patent No.: US 10,140,440 B1
(45) Date of Patent: Nov. 27, 2018

(54) SYSTEMS AND METHODS FOR SECURING COMPUTING DEVICES THAT ARE NOT IN USERS' PHYSICAL POSSESSIONS

(71) Applicant: Symantec Corporation, Mountain View, CA (US)

(72) Inventors: Keith Newstadt, Newton, MA (US); Ilya Sokolov, Boston, MA (US)

(73) Assignee: Symantec Corporation, Mountain View, CA (US)

( * ) Notice: Subject to any disclaimer, the term of this patent is extended or adjusted under 35 U.S.C. 154(b) by 126 days.

(21) Appl. No.: 15/376,968

(22) Filed: Dec. 13, 2016

(51) Int. Cl.
*G06F 21/34* (2013.01)
*G06F 21/32* (2013.01)
*G01N 27/02* (2006.01)
*G01N 27/72* (2006.01)
*G06F 21/62* (2013.01)
*A61B 5/024* (2006.01)
*A61B 5/103* (2006.01)
*A61B 5/107* (2006.01)
(Continued)

(52) U.S. Cl.
CPC .......... *G06F 21/32* (2013.01); *A61B 5/02438* (2013.01); *A61B 5/1032* (2013.01); *A61B 5/1075* (2013.01); *A61B 5/165* (2013.01); *A61B 5/4875* (2013.01); *G01N 27/028* (2013.01); *G01N 27/72* (2013.01); *G06F 21/34* (2013.01); *G06F 21/62* (2013.01)

(58) Field of Classification Search
CPC .......... G06F 21/32; G06F 21/34; G06F 21/62; G01N 27/028; G01N 27/72; A61B 5/02438; A61B 5/1032; A61B 5/1075; A61B 5/165; A61B 5/4875
See application file for complete search history.

(56) References Cited

U.S. PATENT DOCUMENTS

| 8,531,296 | B2 | 9/2013 | Wehrenberg |
| 8,924,736 | B1 * | 12/2014 | Dusan ............... G06F 21/32 340/5.52 |

(Continued)

OTHER PUBLICATIONS

Phil Berardelli; Tapping Tesla to Save Trapped Miners; http://www.sciencemag.org/news/2010/08/tapping-tesla-save-trapped-miners; Aug. 20, 2010.

(Continued)

*Primary Examiner* — Joseph P Hirl
*Assistant Examiner* — Stephen T Gundry
(74) *Attorney, Agent, or Firm* — Fisher Broyles, LLP

(57) ABSTRACT

The disclosed computer-implemented method for securing computing devices that are not in users' physical possessions may include (i) taking, at a computing device of a user while the user is in physical possession of the computing device, a first measurement of a biological attribute of the user's body, (ii) taking, at the computing device, a second measurement of the same biological attribute, (iii) analyzing, at the computing device, the second measurement relative to the first measurement to determine that the user is no longer in physical possession of the computing device, and (iv) performing, at the computing device in response to determining that the user is no longer in physical possession of the computing device, a security action. Various other methods, systems, and computer-readable media are also disclosed.

20 Claims, 8 Drawing Sheets

(51) Int. Cl.
*A61B 5/16* (2006.01)
*A61B 5/00* (2006.01)

(56) References Cited

U.S. PATENT DOCUMENTS

| | | | | |
|---|---|---|---|---|
| 8,938,369 | B1* | 1/2015 | Sobel | G06F 3/015 |
| | | | | 702/182 |
| 9,111,085 | B1* | 8/2015 | Darmour | G06F 21/34 |
| 9,256,766 | B1 | 2/2016 | Newstadt | |
| 9,380,429 | B1* | 6/2016 | Kurani | H04W 4/028 |
| 9,503,452 | B1* | 11/2016 | Kumar | H04L 67/306 |
| 9,544,308 | B2* | 1/2017 | Minter | H04L 63/0861 |
| 9,565,192 | B2* | 2/2017 | Chillappa | H04L 63/102 |
| 9,693,711 | B2* | 7/2017 | Yuen | A61B 5/117 |
| 9,805,213 | B1* | 10/2017 | Kragh | G06F 21/6227 |
| 9,858,781 | B1* | 1/2018 | Campero | G06F 9/451 |
| 9,866,393 | B1* | 1/2018 | Rush | H04L 9/3247 |
| 9,947,008 | B1* | 4/2018 | Camacho Diaz | |
| | | | | G06Q 20/38215 |
| 2005/0281439 | A1* | 12/2005 | Lange | A61B 5/04525 |
| | | | | 382/115 |
| 2008/0086533 | A1* | 4/2008 | Neuhauser | G06Q 10/00 |
| | | | | 709/206 |
| 2008/0146892 | A1* | 6/2008 | LeBoeuf | A61B 5/11 |
| | | | | 600/300 |
| 2010/0207721 | A1* | 8/2010 | Nakajima | G06F 21/552 |
| | | | | 340/5.3 |
| 2013/0019292 | A1* | 1/2013 | Varshavsky | H04L 9/3231 |
| | | | | 726/7 |
| 2013/0102283 | A1 | 4/2013 | Lau et al. | |
| 2013/0332286 | A1* | 12/2013 | Medelius | A61B 5/01 |
| | | | | 705/14.66 |
| 2014/0073486 | A1* | 3/2014 | Ahmed | A61B 5/02405 |
| | | | | 482/9 |
| 2014/0165184 | A1* | 6/2014 | Lange | G06F 21/32 |
| | | | | 726/19 |
| 2015/0143496 | A1* | 5/2015 | Thomas | G06F 21/34 |
| | | | | 726/7 |
| 2015/0180834 | A1* | 6/2015 | Sobel | H04L 63/0421 |
| | | | | 380/255 |
| 2015/0242605 | A1* | 8/2015 | Du | G06F 21/32 |
| | | | | 726/7 |
| 2016/0125412 | A1* | 5/2016 | Cannon | G06Q 20/4014 |
| | | | | 705/44 |
| 2016/0154952 | A1* | 6/2016 | Venkatraman | H04L 63/0861 |
| | | | | 705/44 |
| 2016/0165036 | A1* | 6/2016 | Leow | H04M 1/72527 |
| | | | | 455/557 |
| 2016/0182503 | A1* | 6/2016 | Cheng | H04L 63/0861 |
| | | | | 726/7 |
| 2016/0241402 | A1* | 8/2016 | Gordon | H04L 9/3228 |
| 2016/0261411 | A1* | 9/2016 | Yau | H04L 63/0807 |
| 2016/0269379 | A1* | 9/2016 | Livesay | G06K 9/00288 |
| 2016/0308862 | A1* | 10/2016 | Rolfe | H04L 9/3236 |
| 2017/0020400 | A1* | 1/2017 | Rinderknecht | A61B 5/02416 |
| 2017/0048218 | A1* | 2/2017 | Lindemann | H04L 29/06 |
| 2017/0085568 | A1* | 3/2017 | Rolfe | H04L 63/0884 |
| 2017/0116615 | A1* | 4/2017 | Burgess | G06Q 20/40145 |
| 2017/0200151 | A1* | 7/2017 | Bruno | G06Q 20/363 |
| 2017/0230361 | A1* | 8/2017 | Toth | H04L 63/0861 |
| 2017/0255273 | A1* | 9/2017 | Yuen | G06F 3/017 |
| 2017/0286768 | A1* | 10/2017 | Livesay | G06K 9/00892 |
| 2017/0289120 | A1* | 10/2017 | Kohli | H04L 63/08 |
| 2017/0324750 | A1* | 11/2017 | Khan | H04L 63/123 |
| 2018/0007044 | A1* | 1/2018 | Varshavsky | H04L 9/3231 |
| 2018/0041503 | A1* | 2/2018 | Lindemann | H04L 63/0435 |
| 2018/0042552 | A1* | 2/2018 | Li | A61B 5/686 |
| 2018/0070821 | A1* | 3/2018 | Liebschner | A61B 5/0051 |
| 2018/0077151 | A1* | 3/2018 | Campero | G06F 9/451 |
| 2018/0137512 | A1* | 5/2018 | Georgiadis | H04L 9/3239 |
| 2018/0150647 | A1* | 5/2018 | Naqvi | G06F 21/6218 |
| 2018/0173871 | A1* | 6/2018 | Toth | G06F 21/45 |

OTHER PUBLICATIONS

Yong Song et al.; Signal Transmission in a Human Body Medium-Based Body Sensor Network Using a Mach-Zehnder Electro-Optical Sensor; https://www.ncbi.nlm.nih.gov/pmc/articles/PMC3571797/; Nov. 30, 2012.

Magnetic fields provide a new way to communicate wirelessly; http://jacobsschool.ucsd.edu/news/news_releases/release.sfe?id=1807; Aug. 31, 2015.

Kevin Bostic; Apple granted patent on accelerometer-based anti-theft system; http://appleinsider.com/articles/13/09/11/apple-patents; Sep. 11, 2013.

Apple Invents Facial Recognition Locking & Unlocking System; http://www.patentlyapple.com/patently-apple/2012/09/apple-invents-facial-recognition-locking-unlocking-system.html; Sep. 20, 2012.

* cited by examiner

SYSTEMS AND METHODS FOR SECURING COMPUTING DEVICES THAT ARE NOT IN USERS' PHYSICAL POSSESSIONS

BACKGROUND

Computing devices have become a ubiquitous part of everyday life. For example, most people carry and use personal computing devices (e.g., smartphones and tablets) throughout their daily activities. Unfortunately, computing devices (especially relatively small mobile devices) may be easily lost, temporarily misplaced, left unattended, or stolen. Since considerable amounts of sensitive data and/or services may be accessible through today's computing devices, a typical computing device may provide optional locking mechanisms to reduce the likelihood that an unauthorized user will gain access to the sensitive data and/or services.

Many locking mechanisms are time-based. For example, one common locking mechanism may lock a computing device if a user does not actively use the device for a given period of time. Unfortunately, conventional time-based locking mechanisms may provide poor security in many important scenarios. For example, a locking mechanism that locks a mobile computing device after a user has not actively used the mobile computing device for a relatively long period of time may not be effective if the device is lost, misplaced, or left unattended and then found by an unauthorized user before the period of time has expired. Even if a computing device is locked after a relatively short period of inactivity, such locking mechanisms may not be effective if the device is stolen when the user is actively using the device. In addition to poor security, conventional time-based locking mechanisms may also provide poor usability to many users. For example, users that check their devices frequently may be forced to authenticate many times throughout the day in order to unlock their devices. The instant disclosure, therefore, identifies and addresses a need for systems and methods for securing computing devices that are not in users' physical possessions.

SUMMARY

As will be described in greater detail below, the instant disclosure describes various systems and methods for securing computing devices that are not in users' physical possessions. In one example, a method for securing computing devices that are not in users' physical possessions may include (i) taking, at a computing device of a user while the user is in physical possession of the computing device, a first measurement of a biological attribute of the user's body, (ii) taking, at the computing device, a second measurement of the same biological attribute, (iii) analyzing, at the computing device, the second measurement relative to the first measurement to determine that the user is no longer in physical possession of the computing device, and (iv) performing, at the computing device in response to determining that the user is no longer in physical possession of the computing device, a security action.

In some examples, the step of taking the first measurement may be performed in response to the user unlocking the computing device, and performing the security action may include locking the computing device. In another example, the method may further include (i) configuring the computing device and an additional computing device of the user to exchange trusted heartbeat messages through the user's body, (ii) transmitting, from the additional computing device, a first heartbeat message through the user's body, and (iii) transmitting, from the additional computing device after the first heartbeat message is transmitted, a second heartbeat message through the user's body. In this example, the step of taking the first measurement may include receiving the first heartbeat message through the user's body, the step of taking the second measurement may include (i) attempting to receive the second heartbeat message through the user's body and (ii) failing to receive the second heartbeat message through the user's body, and the step of analyzing the second measurement relative to the first measurement to determine that the user is no longer in physical possession of the computing device may include determining, based at least in part on failing to receive the second heartbeat message through the user's body, that the user is no longer in physical possession of the computing device.

In at least one example, a thief may have stolen the computing device after the first measurement was taken, the second measurement may include a measurement of the same biological attribute of the thief's body, and the step of analyzing the second measurement relative to the first measurement to determine that the user is no longer in physical possession of the computing device may include determining that a difference between the second measurement and the first measurement indicates that the first measurement and the second measurement were taken from different individuals. In some examples, the second measurement may include an attempted measurement of the biological attribute of the user's body, and the step of analyzing the second measurement relative to the first measurement to determine that the user is no longer in physical possession of the computing device may include determining that a difference between the second measurement and the first measurement indicates that the second measurement was taken when the user was no longer in physical possession of the computing device. In various examples, the biological attribute may include an electric signal, an electromagnetic field, a biological heartbeat, a hydration level, a stress level, an electrical impedance, a skin tone, or a skin thickness.

In one embodiment, a system for securing computing devices that are not in users' physical possessions may include a computing device of a user that includes (i) a measuring module, stored in the computing device's memory, that (a) takes, at the computing device while the user is in physical possession of the computing device, a first measurement of a biological attribute of the user's body and (b) takes, at the computing device, a second measurement of the same biological attribute, (ii) an analyzing module, stored in the computing device's memory, that analyzes, at the computing device, the second measurement relative to the first measurement to determine that the user is no longer in physical possession of the computing device, (iii) a security module, stored in the computing device's memory, that performs, at the computing device in response to determining that the user is no longer in physical possession of the computing device, a security action, and (iv) at least one physical processor that executes the measuring module, the analyzing module, and the security module.

In some examples, the system may also include an additional computing device of the user that includes (i) a configuring module, stored in the additional computing device's memory, that configures the additional computing device of the user to exchange trusted heartbeat messages with the computing device through the user's body and (ii) a transmitting module, stored in the additional computing device's memory, that (a) transmits, from the additional computing device, a first heartbeat message through the user's body and (b) transmits, from the additional computing device after the first heartbeat message is transmitted, a second heartbeat message through the user's body. In this example, the measuring module may take the first measurement by receiving the first heartbeat message through the user's body, the measuring module may take the second measurement by (i) attempting to receive the second heartbeat message through the user's body and (ii) failing to receive the second heartbeat message through the user's body, and the analyzing module may analyze the second measurement relative to the first measurement to determine that the user is no longer in physical possession of the computing device by determining, based at least in part on failing to receive the second heartbeat message through the user's body, that the user is no longer in physical possession of the computing device.

In some examples, the above-described method may be encoded as computer-readable instructions on a non-transitory computer-readable medium. For example, a computer-readable medium may include one or more computer-executable instructions that, when executed by at least one processor of a computing device of a user, may cause the computing device to (i) take, at the computing device while the user is in physical possession of the computing device, a first measurement of a biological attribute of the user's body, (ii) take, at the computing device, a second measurement of the same biological attribute, (iii) analyze, at the computing device, the second measurement relative to the first measurement to determine that the user is no longer in physical possession of the computing device, and (iv) perform, at the computing device in response to determining that the user is no longer in physical possession of the computing device, a security action.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of example embodiments and are a part of the specification. Together with the following description, these drawings demonstrate and explain various principles of the instant disclosure.

Figure 1:
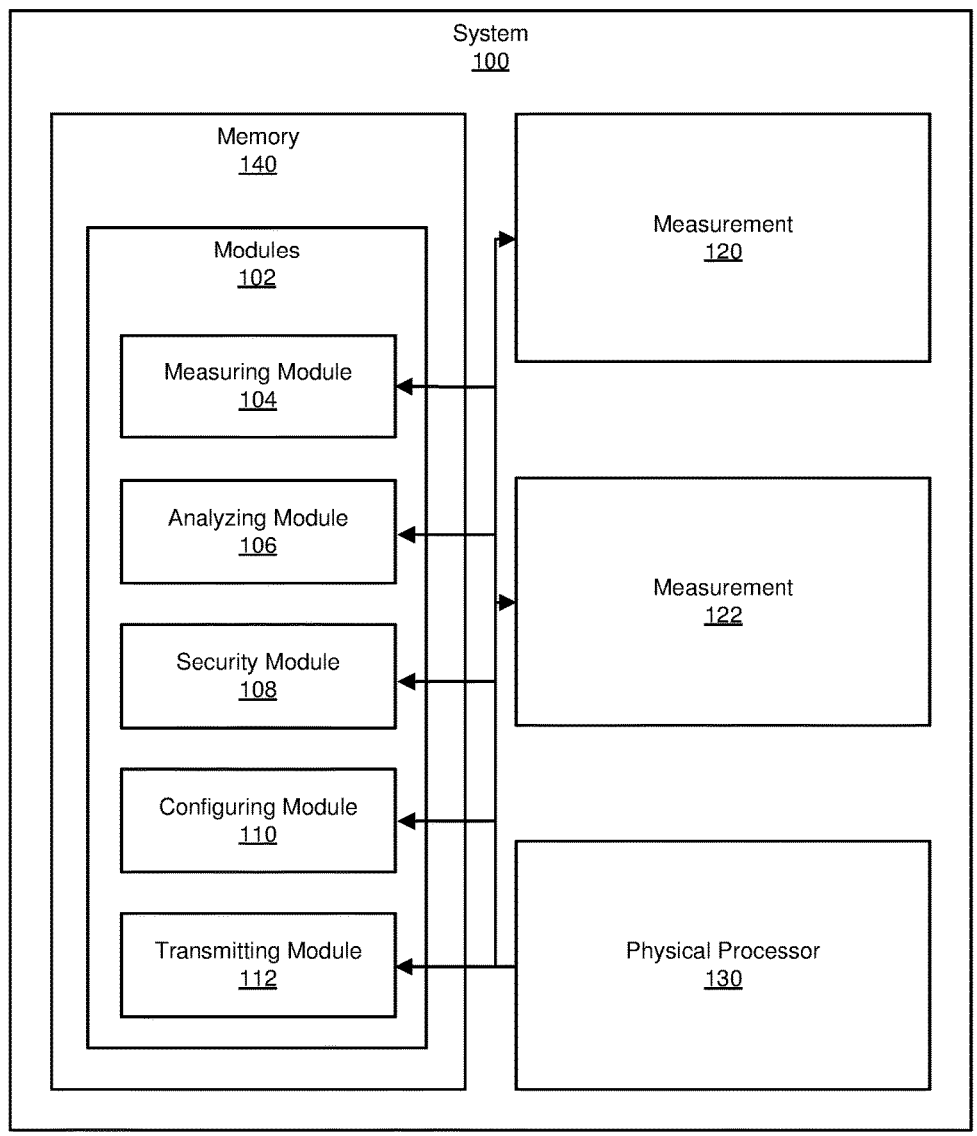
FIG. 1 is a block diagram of an example system for securing computing devices that are not in users' physical possessions.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

The present disclosure is generally directed to systems and methods for securing computing devices that are not in users' physical possessions. As will be explained in greater detail below, by monitoring, at a computing device of an authorized user, biological attributes of the user's body to detect when the user has or has lost physical possession of the computing device, the systems and methods described herein may improve the security of the computing device when the user is no longer in physical possession of the computing device while also improving the usability of the computing device when the user is in physical possession of the computing device. Furthermore, in some examples, by (i) using a user's body to communicatively connect the user's computing devices while the user is in physical possession of the computing devices and (ii) detecting when one or more of the computing devices cannot communicate with the others, these systems and methods may detect when the user has lost physical possession of one or more of the computing devices.

In addition, the systems and methods described herein may improve the functioning of a computing device by enabling the computing device to determine when a user has or has lost physical possession of the computing device, thus reducing the computing device's likelihood of becoming compromised when not in the physical possession of the user and improving the usability of the computing device when in the physical possession of the user. These systems and methods may also improve the field of device security by enabling various security actions to be performed when a user has or has lost physical possession of a computing device. Embodiments of the instant disclosure may also provide various other advantages and features, as discussed in greater detail below.

The following will provide, with reference to FIGS. 1-4, detailed descriptions of example systems for securing computing devices that are not in users' physical possessions. Detailed descriptions of corresponding computer-implemented methods will also be provided in connection with FIGS. 5 and 6. In addition, detailed descriptions of an example computing system and network architecture capable of implementing one or more of the embodiments described herein will be provided in connection with FIGS. 7 and 8, respectively.

FIG. 1 is a block diagram of an example system 100 for securing computing devices that are not in users' physical possessions. As illustrated in this figure, example system 100 may include one or more modules 102 for performing one or more tasks. As will be explained in greater detail below, modules 102 may include a measuring module 104, an analyzing module 106, a security module 108, a configuring module 110, and a transmitting module 112. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, and as will be described in greater detail below, one or more of modules 102 may represent modules stored and configured to run on one or more computing devices, such as the devices illustrated in FIG. 2 (e.g., computing device 202 and/or computing device 206). One or more of modules 102 in FIG. 1 may also represent all or portions of one or more special-purpose computers configured to perform one or more tasks.

As illustrated in FIG. 1, example system 100 may also include one or more memory devices, such as memory 140. Memory 140 generally represents any type or form of volatile or non-volatile storage device or medium capable of storing data and/or computer-readable instructions. In one example, memory 140 may store, load, and/or maintain one or more of modules 102. Examples of memory 140 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 1, example system 100 may also include one or more physical processors, such as physical processor 130. Physical processor 130 generally represents any type or form of hardware-implemented processing unit capable of interpreting and/or executing computer-readable instructions. In one example, physical processor 130 may access and/or modify one or more of modules 102 stored in memory 140. Additionally or alternatively, physical processor 130 may execute one or more of modules 102 to facilitate securing computing devices that are not in users' physical possessions. Examples of physical processor 130 include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, and/or any other suitable physical processor.

As illustrated in FIG. 1, example system 100 may also include one or more measurements, such as measurements 120 and 122. Measurements 120 and 122 generally represent any type or form of a reading of a biological attribute of a person's body. In one example, measurements 120 and 122 may represent measurements of magnetic or electrical signals that are transmitted through a person's body and that may contain heartbeat messages. In some examples, measurements 120 and 122 may represent measurements obtained from an electric-field sensor, a magnetic-field sensor, a heartbeat sensor, a hydration-level sensor, a stress-level sensor, an electrical-impedance sensor, a skin-tone sensor, or a skin-thickness sensor.

Figure 2:
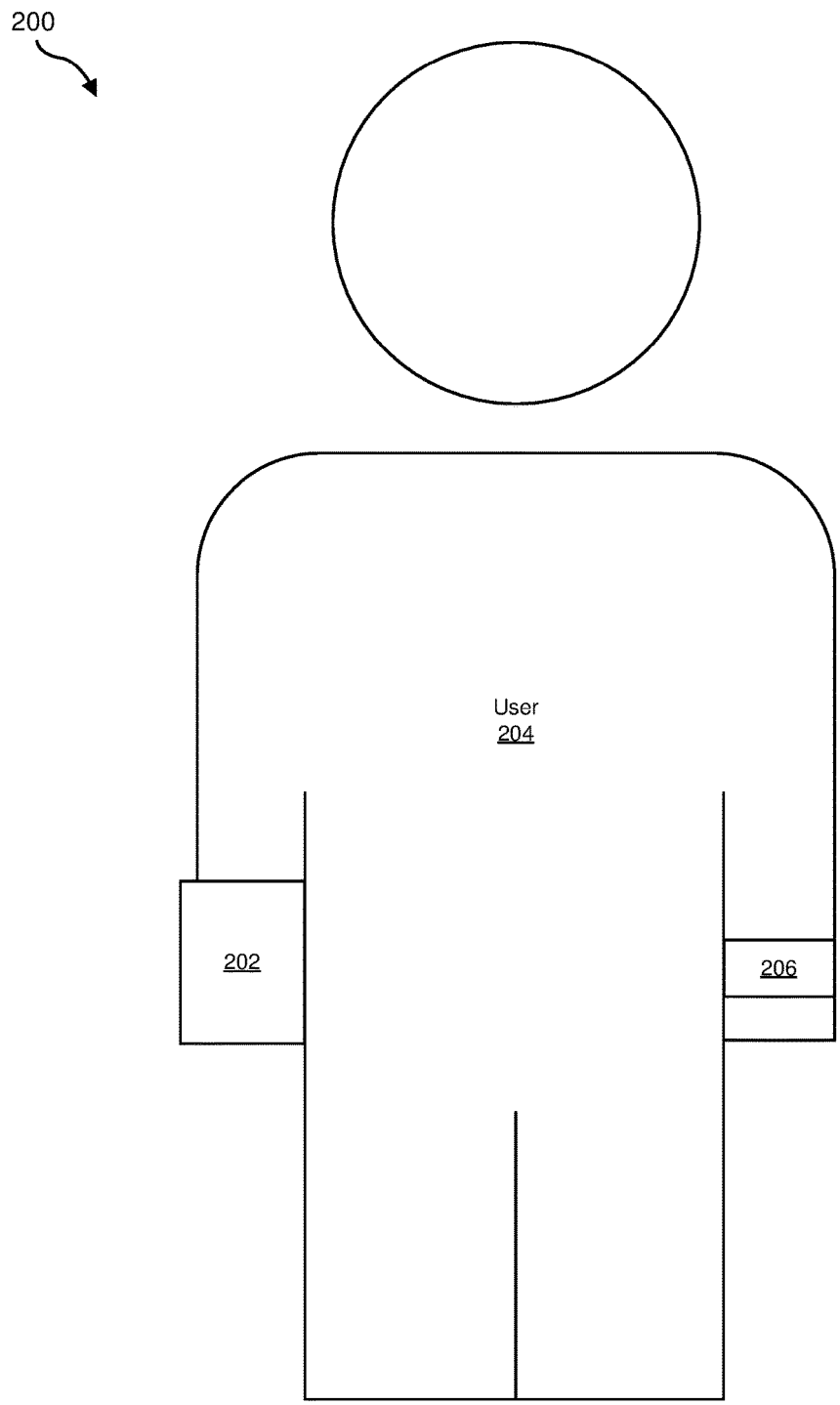
FIG. 2 is a block diagram of an example system for securing computing devices that are not in users' physical possessions.
Figure 3:
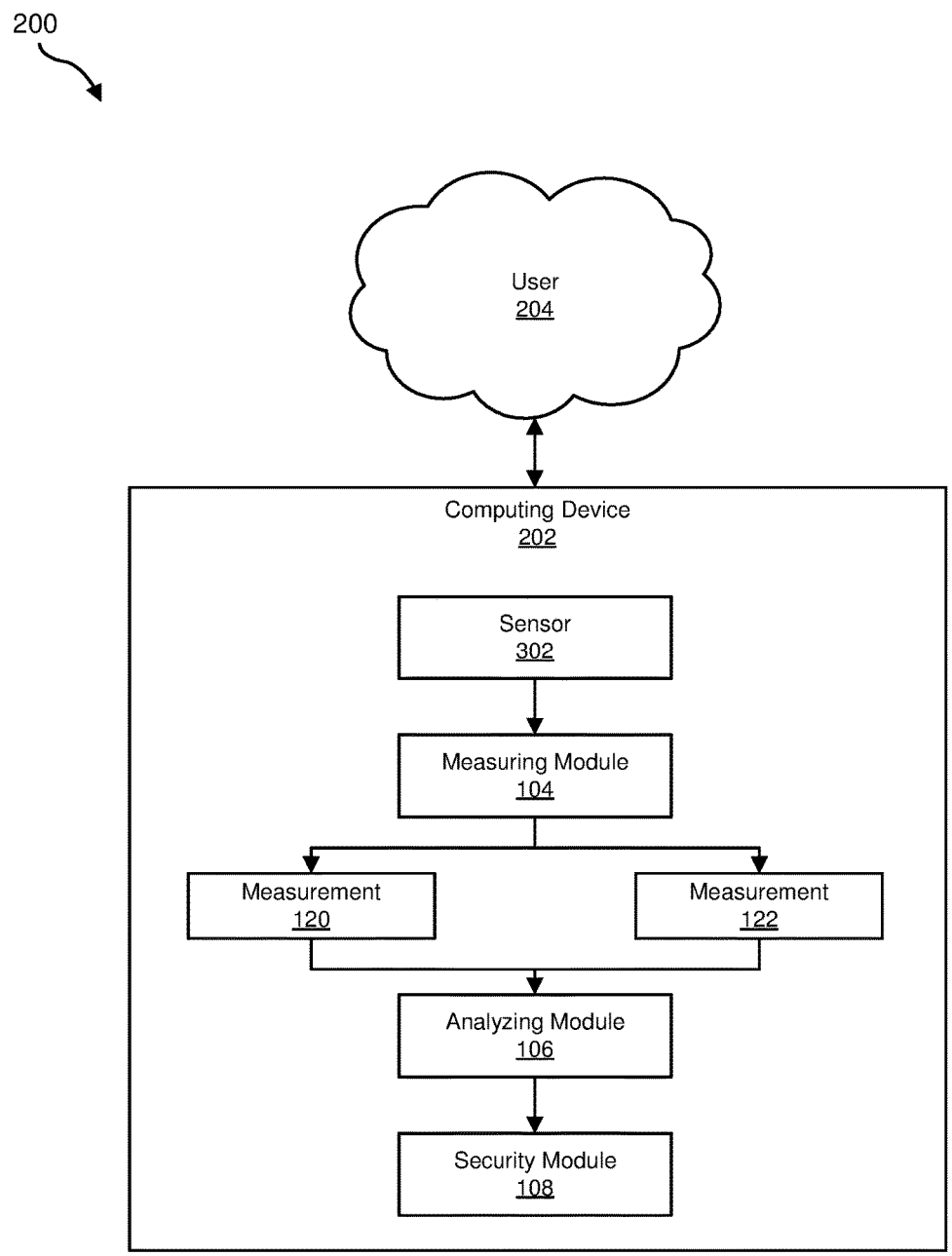
FIG. 3 is a block diagram of an example system for securing computing devices that are not in users' physical possessions.
Figure 4:
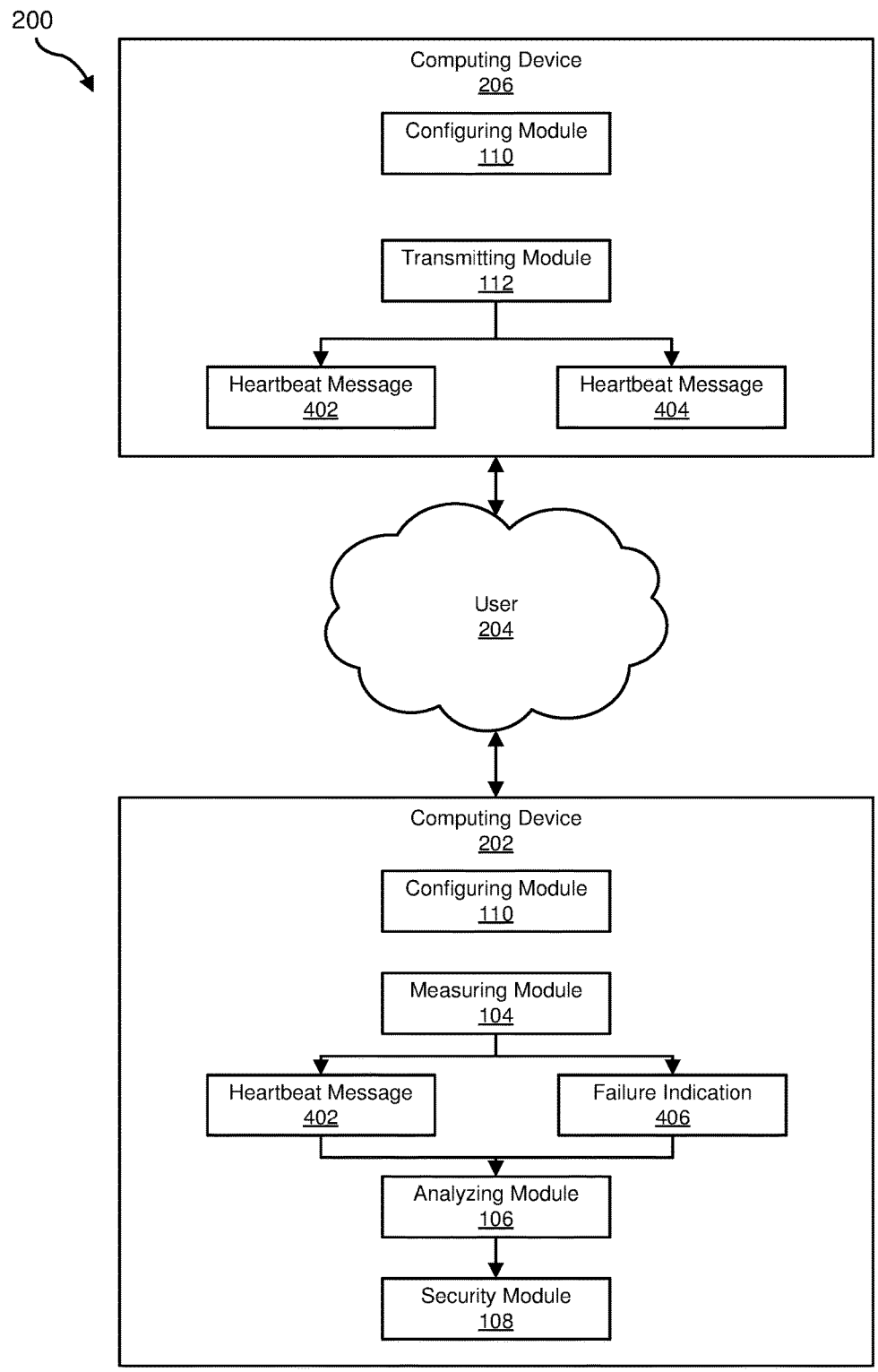
FIG. 4 is a block diagram of an example system for securing computing devices that are not in users' physical possessions.

Example system 100 in FIG. 1 may be implemented in a variety of ways. For example, all or a portion of example system 100 may represent portions of example system 200 in FIGS. 2-4. As shown in FIGS. 2-4, system 200 may include a computing device 202 and/or a computing device 206 of a user 204 that may, at times, be in the physical possession of user 204. In one example, all or a portion of the functionality of modules 102 may be performed by computing device 202, computing device 206, and/or any other suitable computing system. As will be described in greater detail below, one or more of modules 102 from FIG. 1 may, when executed by at least one processor of computing device 202 and/or computing device 206, enable computing device 202 and/or computing device 206 to secure computing devices 202 and/or 206 when computing devices 202 and/or 206 are no longer in the physical possession of user 204. For example, and as will be described in greater detail below, one or more of modules 102 may cause computing device 202 to (i) take, at computing device 202 while user 204 is in physical possession of computing device 202, a measurement 120 of a biological attribute of user 204, (ii) take, at computing device 202, a measurement 122 of the same biological attribute, (iii) analyze, at computing device 202, measurement 122 relative to measurement 120 to determine whether user 204 is in physical possession of computing device 202, and (iv) perform, at computing device 202 in response to determining that user 204 is no longer in physical possession of computing device 202, a security action.

Computing devices 202 and 206 generally represent any type or form of computing device that is capable of reading computer-executable instructions. Examples of computing devices 202 and 206 include, without limitation, laptops, desktops, tablets, e-readers, cellular phones, smart phones, Personal Digital Assistants (PDAs), multimedia players, wearable devices (e.g., smart watches, smart glasses, smart jewelry, smart shoes, etc.), gaming consoles, keys, key fobs, and/or combinations of one or more of the same. As illustrated in FIG. 3, in some examples, computing device 202 may include one or more sensors, such as sensor 302, for measuring biological attributes. Examples of sensor 302 include, without limitation, electric-field sensors for measuring electric fields that pass through a user's body, magnetic-field sensors for measuring magnetic fields that pass through a user's body, heartbeat sensors for measuring a physical heartbeat of a user, hydration-level sensors for measuring hydration levels of a user's body, stress-level sensors for measuring stress levels of a user's body, electrical-impedance sensors for measuring electrical impedances of a user's body, skin-tone sensors for measuring the skin tone of a user, or skin-thickness sensors for measuring the thickness of a user's skin. In at least one example, sensor 302 may represent a receiver of wireless electromagnetic signals that can distinguish electromagnetic signals that are transmitted along a path that passes through a person's body from electromagnetic signals that are not transmitted along a path that passes through the person's body.

User 204 generally represents the physical body of an owner or authorized user of computing devices 202 and/or 206. In one example, user 204 may facilitate communication between computing device 202 and computing device 206. For example, as illustrated in FIG. 4, user 204 may facilitate the exchange of heartbeat messages, such as heartbeat message 402 or heartbeat message 404, between computing device 202 and computing device 206. In some examples, computing device 202 and/or computing device 206 may exchange heartbeat messages using magnetic and/or electric fields that pass through user 204.

Figure 5:
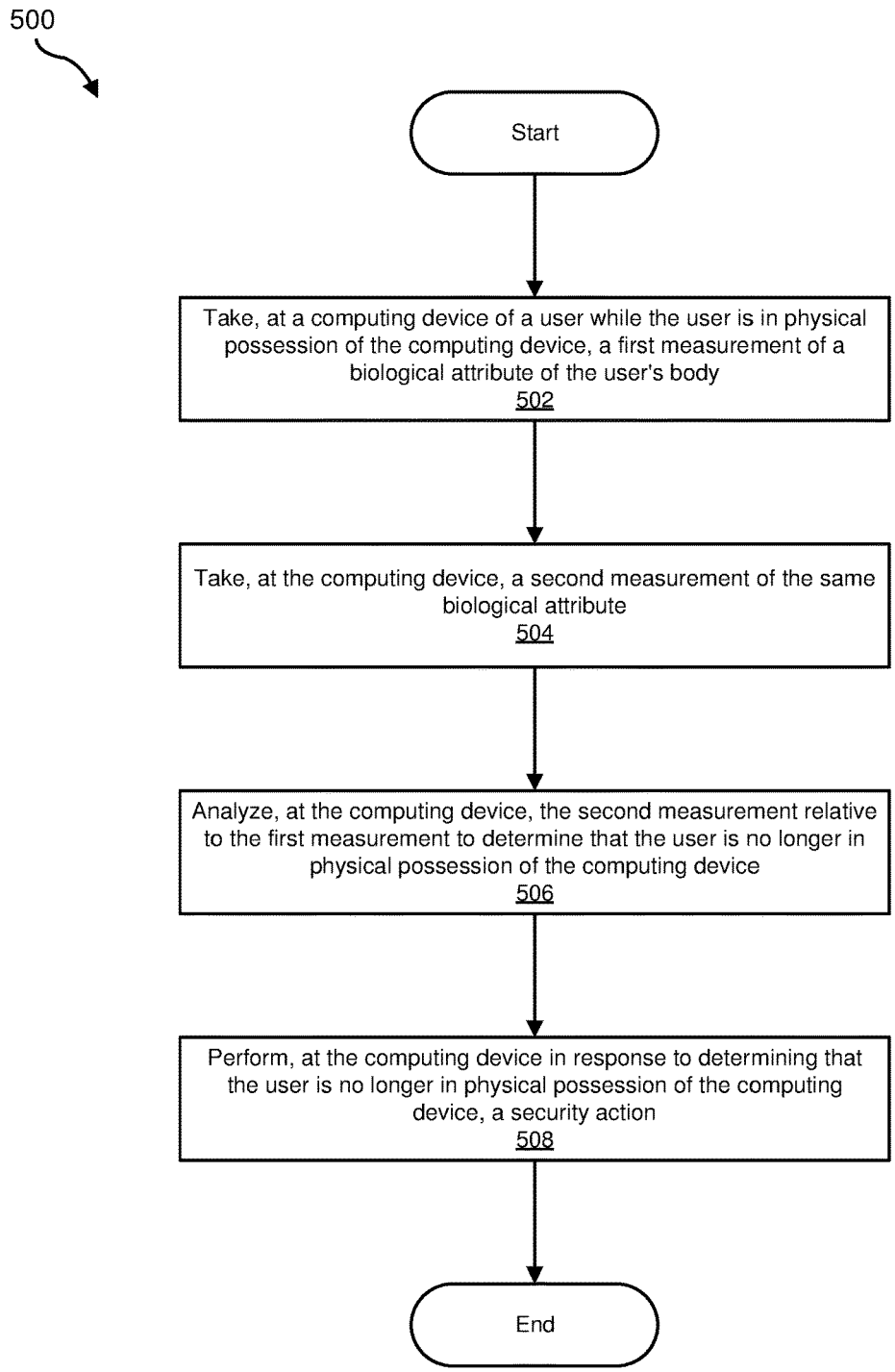
FIG. 5 is a flow diagram of an example method for securing computing devices that are not in users' physical possessions.
Figure 6:
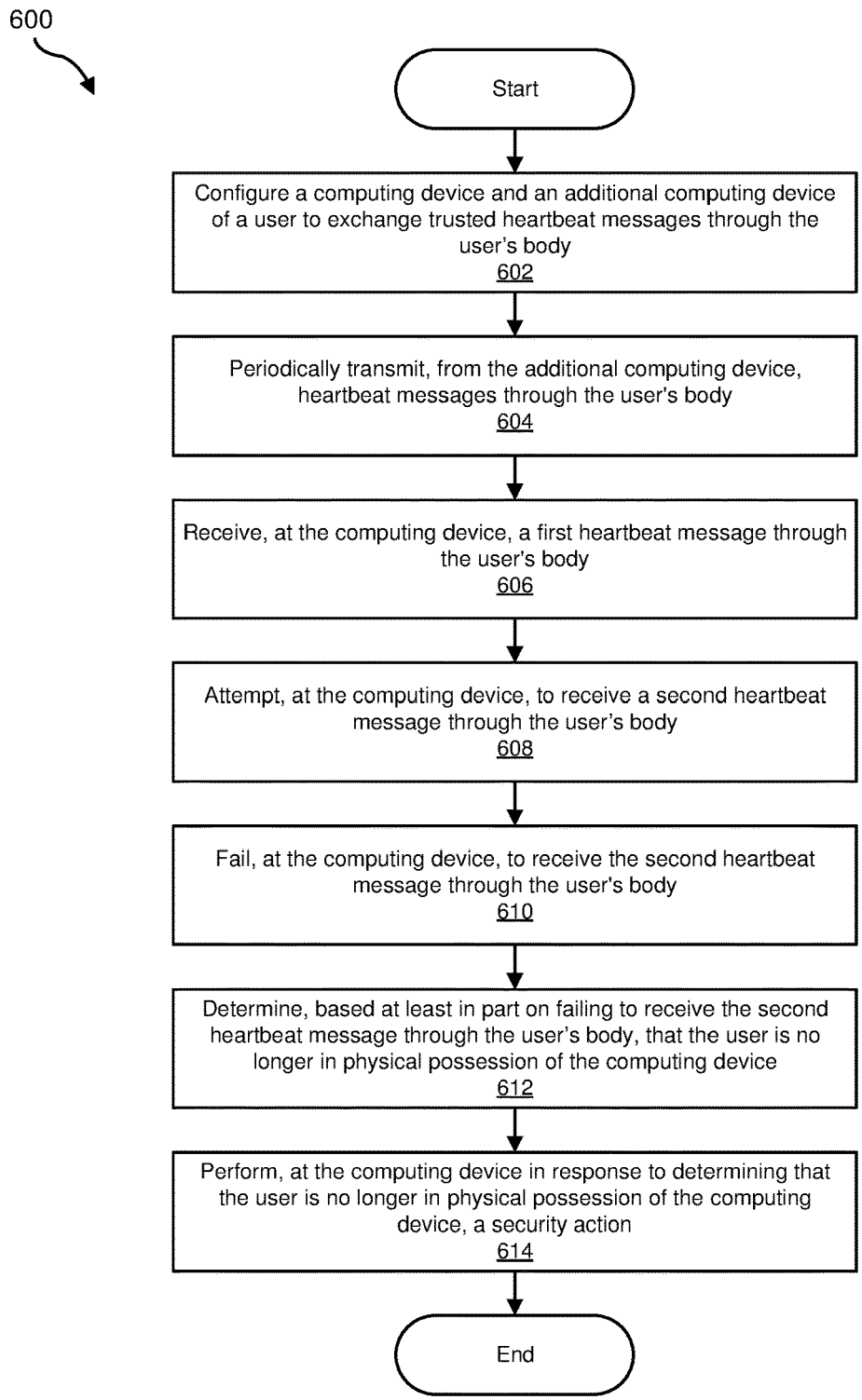
FIG. 6 is a flow diagram of an example method for securing computing devices that are not in users' physical possessions.

FIG. 5 is a flow diagram of an example computer-implemented method 500 for securing computing devices that are not in users' physical possessions. FIG. 6 is a flow diagram of another example computer-implemented method 600 for securing computing devices that are not in users' physical possessions. Computer-implemented method 600 in FIG. 6 may represent one implementation of computer-implemented method 500 in FIG. 5. The steps shown in FIGS. 5 and 6 may be performed by any suitable computer-executable code and/or computing system, including system 100 in FIG. 1, system 200 in FIGS. 2-4, and/or variations or combinations of one or more of the same. In one example, each of the steps shown in FIG. 5 or FIG. 6 may represent an algorithm whose structure includes and/or is represented by multiple sub-steps, examples of which will be provided in greater detail below.

As illustrated in FIG. 5, at step 502 one or more of the systems described herein may take, at a computing device of a user while the user is in physical possession of the computing device, a first measurement of a biological attribute of the user's body. For example, measuring module 104 may, as part of computing device 202 in FIG. 2, take a measurement 120 of a biological attribute of user 204 while user 204 is in physical possession of computing device 202.

Measuring module 104 may take, as part of a computing device, measurements of a variety of biological attributes of a person that possesses the computing device using any suitable sensor or receiver. As used herein, the term "biological attribute" generally refers to any characteristic of a person's body that can be measured at a computing device when the computing device is in the person's physical possession. Examples of biological attributes of a person include, without limitation, electrical signals that pass through the person's body, electromagnetic fields (e.g., wireless communication signals) that pass through the person's body, the person's biological heartbeat, a hydration level of the person's body, a stress level of the person's body, an electrical impedance of the person's body, the person's skin tone, the person's skin thickness, the person's weight, the person's eye color, the person's hair color, the person's body temperature, and the person's body scent. A computing device may be considered to be in a person's physical possession if the computing device is in physical contact with the person's body (e.g., the computing device is in a hand of the person, is being worn by the person, or is being carried by the person), if the computing device is close enough to the person's body such that a biological attribute of the person's body may be measured at the computing device, and/or if the computing device is close enough to the user such that heartbeat messages may be transmitted and/or received through the person's body.

In some examples, measuring module 104 may begin measuring, at a computing device, biological attributes of a person when the computing device is first unlocked. By beginning to measure the biological attributes of a person when a computing device is unlocked, the systems and methods disclosed herein may assume that the biological attributes of an owner or an authorized person of the computing device are being measured. Additionally or alternatively, measuring module 104 may begin measuring biological attributes of a person when the person begins to actively use a computing device.

In some examples (as indicated at step 602 in FIG. 6), configuring module 110 may configure a person's computing devices to exchange heartbeat messages through the person's body via electromagnetic fields or electrical impulses. In these examples (as indicated at steps 604 and 606), transmitting module 112 may, as part of one of the person's computing devices, periodically transmit heartbeat messages through the person's body, and measuring module 104 may receive a first heartbeat message by detecting, at another computing device of the person, an electrical signal or an electromagnetic field that carries the first heartbeat message as it passes or after it passes through the person's body. Using FIG. 4 as an example, transmitting module 112 may, as part of computing device 206 in FIG. 4, transmit heartbeat message 402 through user 204, and measuring module 104 may, as part of computing device 202, receive heartbeat message 402 through user 204.

In some examples, configuring module 110 may configure a person's computing devices to exchange heartbeat messages through the person's body by creating a trusted network of the computing devices. As will be explained below, when one of the computing devices leaves the trusted network (e.g., a computing device no longer receives heartbeat messages through the person's body), the systems and methods described herein may determine that the person is no longer in physical possession of the computing device and may perform a security action in response.

In some examples, configuring module 110 may configure a person's computing devices to exchange trusted heartbeat messages through the person's body by creating trusted relationships between the person's computing devices such that messages exchanged between the computing devices can be trusted (e.g., by sharing a cryptographic key from which heartbeat messages may be derived and validated). In one example, configuring module 110 may create a trusted relationship between two or more computing devices of a person after prompting, at one of the two or more computing devices, the person to trust the other computing devices (e.g., by requiring the person to enter a code or password displayed on the other computing devices).

Returning to FIG. 5 at step 504, one or more of the systems described herein may take, at the computing device, a second measurement of the same biological attribute. For example, measuring module 104 may, as part of computing device 202 in FIG. 2, take measurement 122 of the same biological attribute that was measured at step 502.

The systems described herein may perform step 504 in any suitable manner. In general, measuring module 104 may periodically take additional measurements of the biological attributes that were measured at step 502 in the same manner in which the measurements were taken at step 502. As will be explained in greater detail below, the systems and methods described herein may determine if a person is still in physical possession of a computing device by comparing the measurements taken at step 502 when the person was in physical possession of the computing device with the measurements taken at step 504 when the person may no longer be in physical possession of the computing device.

In some examples, the person from which measuring module 104 took measurements at step 502 may still be in possession of the computing device when measuring module 104 retakes the same measurements at step 504. For example, measuring module 104 may have taken measurements from an owner of a computing device at step 502 and then retaken the same measurements from the owner at step 504. In examples such as these, the measurements taken at steps 502 and 504 will be from the same person and may be the same or similar.

In other examples, the person from which measuring module 104 took measurements at step 502 may not be the same person from which measuring module 104 takes measurements at step 504. For example, measuring module 104 may have taken measurements from an owner of a computing device at step 502 and then retaken the same measurements from a thief of the computing device at step 504. In examples such as these, the measurements taken at steps 502 and 504 will be from different people and may be considerably different.

In other examples, no person may be in physical possession of a computing device when measuring module 104 attempts to take measurements at step 504. For example, measuring module 104 may have taken measurements from an owner of a computing device at step 502 and then attempted to retake the same measurements at step 504 after the owner has misplaced the computing device or after the owner has left the computing device unattended. In examples such as these, the measurements taken at step 504 may be invalid or outside of typical ranges measured from a person.

In some examples, as mentioned above, configuring module 110 may have configured a person's computing devices to periodically exchange heartbeat messages through the person's body via electromagnetic fields or electrical impulses. So long as two of the computing devices remain in the person's physical possession, measuring module 104 may, as part of one of the computing devices, receive the heartbeat messages that are broadcast by the other computing device. However as indicated at steps 608 and 610 in FIG. 6, when one of the computing devices is no longer in the person's physical possession, measuring module 104 may no longer be able to measure the electromagnetic fields or electrical impulses that pass through the person's body and that carry the heartbeat messages that are broadcast by the other computing devices. As a result, measuring module 104 may fail to receive the heartbeat messages at the computing device. Using FIG. 4 as an example, so long as computing device 202 remains in the physical possession of user 204, measuring module 104 may, as part of computing device 202, receive heartbeat messages that are broadcast by computing device 206. However, when computing device 202 is no longer in the physical possession of user 204, measuring module 104 may, as part of computing device 202, fail to receive the heartbeat messages that are broadcast by computing device 206.

At step 506, one or more of the systems described herein may analyze, at the computing device, the second measurement relative to the first measurement to determine that the user is no longer in physical possession of the computing device. For example, analyzing module 106 may, as part of computing device 202 in FIG. 2, analyze measurement 120 relative to measurement 122 to determine that user 204 is no longer in physical possession of computing device 202.

The systems described herein may perform step 506 in any suitable manner. In some examples, analyzing module 106 may, as part of a computing device, determine whether the person from which measuring module 104 took measurements at step 502 is or is not still in physical possession of the computing device by determining whether a difference between the measurements taken at step 502 and the measurements taken at step 504 indicates that the measurements taken at steps 502 and 504 were taken from different people. For example, analyzing module 106 may, as part of a computing device, determine that the person from which measuring module 104 took measurements at step 502 is still in physical possession of the computing device by determining that the measurements taken at step 502 are the same or similar to the measurements taken at step 504. Alternatively, analyzing module 106 may, as part of a computing device, determine that the person from which measuring module 104 took measurements at step 502 is no longer in physical possession of the computing device by determining that the measurements taken at step 502 and the measurements taken at step 504 are different or by determining that a difference between the measurements exceeds a predetermined threshold. In at least one example, analyzing module 106 may, as part of a computing device, determine that the person from which measuring module 104 took measurements at step 502 is no longer in physical possession of the computing device by determining that the measurements taken at step 504 are invalid or are outside of typical ranges measured from a person.

In some examples, as mentioned above, configuring module 110 may have configured a person's computing devices to periodically exchange heartbeat messages through the person's body via electromagnetic fields or electrical impulses. In these examples as indicated at step 612 in FIG. 6, analyzing module 106 may determine that one of the computing devices is no longer in the person's physical possession if the computing device has failed to receive an expected heartbeat message through the person's body.

At step 508, one or more of the systems described herein may perform, at the computing device in response to determining that the user is no longer in physical possession of the computing device, a security action. For example, security module 108 may, as part of computing device 202 in FIG. 2, perform a security action in response to determining that user 204 is no longer in physical possession of computing device 202.

The systems described herein may perform a variety of security actions in response to determining that a person no longer has physical possession of a computing device. For example, security module 108 may automatically lock a computing device when a person loses physical possession of the computing device. Additionally or alternatively, security module 108 may elevate an authentication policy used to unlock the computing device when the person loses physical possession of the computing device. In this example, when the computing device was initially unlocked and while the computing device remained in the person's physical possession, the systems and methods described herein may have initiated a weaker authentication policy (e.g., using face recognition for authentication rather than a passcode) at the computing device to allow the person to authenticate more easily.

In other examples, security module 108 may cause a computing device to sound an alert or an alarm when a person loses physical possession of the device. In some examples, such an alert or alarm may cause a thief of the computing device to relinquish the computing device and/or may prevent the person from misplacing the computing device or leaving the computing device unattended. Other security actions that security module 108 may perform in response to a person losing physical possession of a computing device may include causing the computing device to shutdown, causing the computing device to erase its memory, and/or causing the computing device to report its location. Upon completion of step 508, exemplary method 500 in FIG. 5 may terminate. Step 614 in FIG. 6 is similar to step 508 in FIG. 5, therefore, the discussion of step 508 may also apply to step 614.

As explained above, by monitoring, at a computing device of an authorized user, biological attributes of the user's body to detect when the user has or has lost physical possession of the computing device, the systems and methods described herein may improve the security of the computing device when the user is no longer in physical possession of the computing device while also improving the usability of the computing device when the user is in physical possession of the computing device. Furthermore, in some examples, by (i) using a user's body to communicatively connect the user's computing devices while the user is in physical possession of the computing devices and (ii) detecting when one or more of the computing devices cannot communicate with the others, these systems and methods may detect when the user has lost physical possession of one or more of the computing devices.

Figure 7:
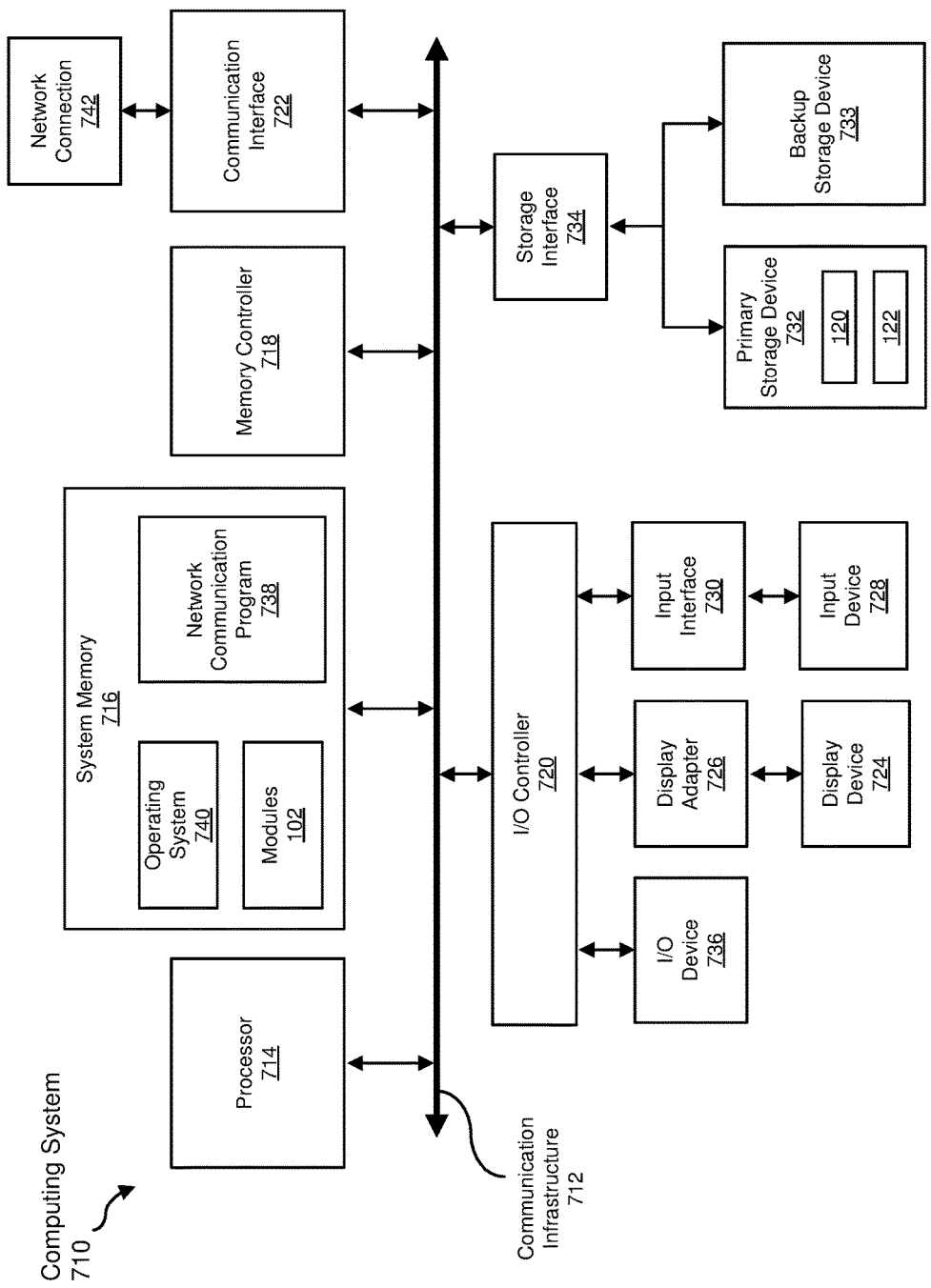
FIG. 7 is a block diagram of an example computing system capable of implementing one or more of the embodiments described and/or illustrated herein.

FIG. 7 is a block diagram of an example computing system 710 capable of implementing one or more of the embodiments described and/or illustrated herein. For example, all or a portion of computing system 710 may perform and/or be a means for performing, either alone or in combination with other elements, one or more of the steps described herein (such as one or more of the steps illustrated in FIG. 5). All or a portion of computing system 710 may also perform and/or be a means for performing any other steps, methods, or processes described and/or illustrated herein.

Computing system 710 broadly represents any single or multi-processor computing device or system capable of executing computer-readable instructions. Examples of computing system 710 include, without limitation, workstations, laptops, client-side terminals, servers, distributed computing systems, handheld devices, or any other computing system or device. In its most basic configuration, computing system 710 may include at least one processor 714 and a system memory 716.

Processor 714 generally represents any type or form of physical processing unit (e.g., a hardware-implemented central processing unit) capable of processing data or interpreting and executing instructions. In certain embodiments, processor 714 may receive instructions from a software application or module. These instructions may cause processor 714 to perform the functions of one or more of the example embodiments described and/or illustrated herein.

System memory 716 generally represents any type or form of volatile or non-volatile storage device or medium capable of storing data and/or other computer-readable instructions. Examples of system memory 716 include, without limitation, Random Access Memory (RAM), Read Only Memory (ROM), flash memory, or any other suitable memory device. Although not required, in certain embodiments computing system 710 may include both a volatile memory unit (such as, for example, system memory 716) and a non-volatile storage device (such as, for example, primary storage device 732, as described in detail below). In one example, one or more of modules 102 from FIG. 1 may be loaded into system memory 716.

In some examples, system memory 716 may store and/or load an operating system 740 for execution by processor 714. In one example, operating system 740 may include and/or represent software that manages computer hardware and software resources and/or provides common services to computer programs and/or applications on computing system 710. Examples of operating system 640 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 710 may also include one or more components or elements in addition to processor 714 and system memory 716. For example, as illustrated in FIG. 7, computing system 710 may include a memory controller 718, an Input/Output (I/O) controller 720, and a communication interface 722, each of which may be interconnected via a communication infrastructure 712. Communication infrastructure 712 generally represents any type or form of infrastructure capable of facilitating communication between one or more components of a computing device. Examples of communication infrastructure 712 include, without limitation, a communication bus (such as an Industry Standard Architecture (ISA), Peripheral Component Interconnect (PCI), PCI Express (PCIe), or similar bus) and a network.

Memory controller 718 generally represents any type or form of device capable of handling memory or data or controlling communication between one or more components of computing system 710. For example, in certain embodiments memory controller 718 may control communication between processor 714, system memory 716, and I/O controller 720 via communication infrastructure 712.

I/O controller 720 generally represents any type or form of module capable of coordinating and/or controlling the input and output functions of a computing device. For example, in certain embodiments I/O controller 720 may control or facilitate transfer of data between one or more elements of computing system 710, such as processor 714, system memory 716, communication interface 722, display adapter 726, input interface 730, and storage interface 734.

As illustrated in FIG. 7, computing system 710 may also include at least one display device 724 coupled to I/O controller 720 via a display adapter 726. Display device 724 generally represents any type or form of device capable of visually displaying information forwarded by display adapter 726. Similarly, display adapter 726 generally represents any type or form of device configured to forward graphics, text, and other data from communication infrastructure 712 (or from a frame buffer, as known in the art) for display on display device 724.

As illustrated in FIG. 7, example computing system 710 may also include at least one input device 728 coupled to I/O controller 720 via an input interface 730. Input device 728 generally represents any type or form of input device capable of providing input, either computer or human generated, to example computing system 710. Examples of input device 728 include, without limitation, a keyboard, a pointing device, a speech recognition device, variations or combinations of one or more of the same, and/or any other input device.

Additionally or alternatively, example computing system 710 may include additional I/O devices. For example, example computing system 710 may include I/O device 736. In this example, I/O device 736 may include and/or represent a user interface that facilitates human interaction with computing system 710. Examples of I/O device 736 include, without limitation, a computer mouse, a keyboard, a monitor, a printer, a modem, a camera, a scanner, a microphone, a touchscreen device, variations or combinations of one or more of the same, and/or any other I/O device.

Communication interface 722 broadly represents any type or form of communication device or adapter capable of facilitating communication between example computing system 710 and one or more additional devices. For example, in certain embodiments communication interface 722 may facilitate communication between computing system 710 and a private or public network including additional computing systems. Examples of communication interface 722 include, without limitation, a wired network interface (such as a network interface card), a wireless network interface (such as a wireless network interface card), a modem, and any other suitable interface. In at least one embodiment, communication interface 722 may provide a direct connection to a remote server via a direct link to a network, such as the Internet. Communication interface 722 may also indirectly provide such a connection through, for example, a local area network (such as an Ethernet network), a personal area network, a telephone or cable network, a cellular telephone connection, a satellite data connection, or any other suitable connection.

In certain embodiments, communication interface 722 may also represent a host adapter configured to facilitate communication between computing system 710 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 722 may also allow computing system 710 to engage in distributed or remote computing. For example, communication interface 722 may receive instructions from a remote device or send instructions to a remote device for execution.

In some examples, system memory 716 may store and/or load a network communication program 738 for execution by processor 714. In one example, network communication program 738 may include and/or represent software that enables computing system 710 to establish a network connection 742 with another computing system (not illustrated in FIG. 7) and/or communicate with the other computing system by way of communication interface 722. In this example, network communication program 738 may direct the flow of outgoing traffic that is sent to the other computing system via network connection 742. Additionally or alternatively, network communication program 738 may direct the processing of incoming traffic that is received from the other computing system via network connection 742 in connection with processor 714.

Although not illustrated in this way in FIG. 7, network communication program 738 may alternatively be stored and/or loaded in communication interface 722. For example, network communication program 738 may include and/or represent at least a portion of software and/or firmware that is executed by a processor and/or Application Specific Integrated Circuit (ASIC) incorporated in communication interface 722.

As illustrated in FIG. 7, example computing system 710 may also include a primary storage device 732 and a backup storage device 733 coupled to communication infrastructure 712 via a storage interface 734. Storage devices 732 and 733 generally represent any type or form of storage device or medium capable of storing data and/or other computer-readable instructions. For example, storage devices 732 and 733 may be a magnetic disk drive (e.g., a so-called hard drive), a solid state drive, a floppy disk drive, a magnetic tape drive, an optical disk drive, a flash drive, or the like. Storage interface 734 generally represents any type or form of interface or device for transferring data between storage devices 732 and 733 and other components of computing system 710. In one example, measurements 120 and/or 122 from FIG. 1 may be stored and/or loaded in primary storage device 732.

In certain embodiments, storage devices 732 and 733 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 732 and 733 may also include other similar structures or devices for allowing computer software, data, or other computer-readable instructions to be loaded into computing system 710. For example, storage devices 732 and 733 may be configured to read and write software, data, or other computer-readable information. Storage devices 732 and 733 may also be a part of computing system 710 or may be a separate device accessed through other interface systems.

Many other devices or subsystems may be connected to computing system 710. Conversely, all of the components and devices illustrated in FIG. 7 need not be present to practice the embodiments described and/or illustrated herein. The devices and subsystems referenced above may also be interconnected in different ways from that shown in FIG. 7. Computing system 710 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 710. All or a portion of the computer program stored on the computer-readable medium may then be stored in system memory 716 and/or various portions of storage devices 732 and 733. When executed by processor 714, a computer program loaded into computing system 710 may cause processor 714 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 710 may be configured as an Application Specific Integrated Circuit (ASIC) adapted to implement one or more of the example embodiments disclosed herein.

Figure 8:
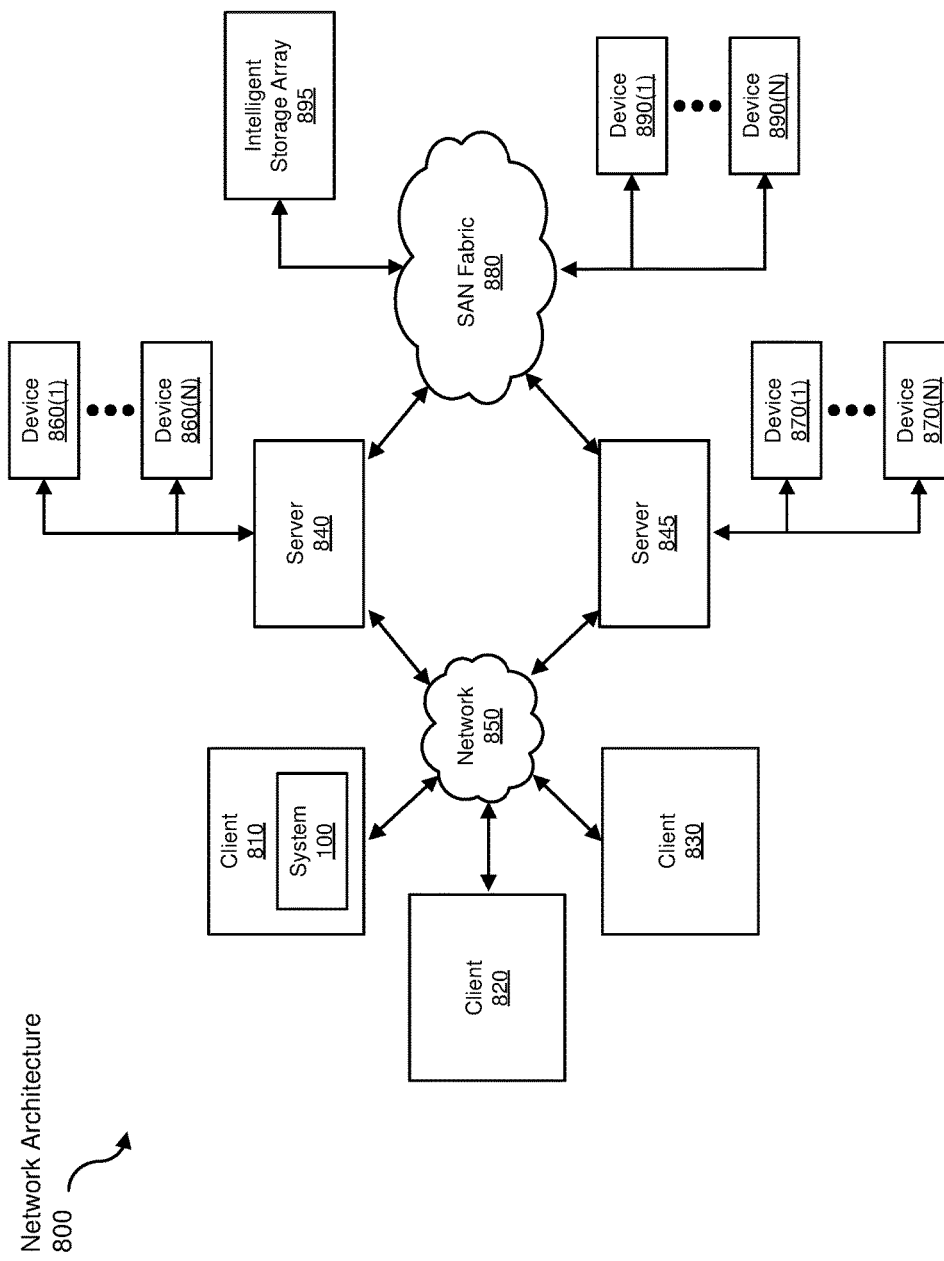
FIG. 8 is a block diagram of an example computing network capable of implementing one or more of the embodiments described and/or illustrated herein.

FIG. 8 is a block diagram of an example network architecture 800 in which client systems 810, 820, and 830 and servers 840 and 845 may be coupled to a network 850. As detailed above, all or a portion of network architecture 800 may perform and/or be a means for performing, either alone or in combination with other elements, one or more of the steps disclosed herein (such as one or more of the steps illustrated in FIG. 5). All or a portion of network architecture 800 may also be used to perform and/or be a means for performing other steps and features set forth in the instant disclosure.

Client systems 810, 820, and 830 generally represent any type or form of computing device or system, such as example computing system 710 in FIG. 7. Similarly, servers 840 and 845 generally represent computing devices or systems, such as application servers or database servers, configured to provide various database services and/or run certain software applications. Network 850 generally represents any telecommunication or computer network including, for example, an intranet, a WAN, a LAN, a PAN, or the Internet. In one example, client systems 810, 820, and/or 830 and/or servers 840 and/or 845 may include all or a portion of system 100 from FIG. 1.

As illustrated in FIG. 8, one or more storage devices 860(1)-(N) may be directly attached to server 840. Similarly, one or more storage devices 870(1)-(N) may be directly attached to server 845. Storage devices 860(1)-(N) and storage devices 870(1)-(N) generally represent any type or form of storage device or medium capable of storing data and/or other computer-readable instructions. In certain embodiments, storage devices 860(1)-(N) and storage devices 870(1)-(N) may represent Network-Attached Storage (NAS) devices configured to communicate with servers 840 and 845 using various protocols, such as Network File System (NFS), Server Message Block (SMB), or Common Internet File System (CIFS).

Servers 840 and 845 may also be connected to a Storage Area Network (SAN) fabric 880. SAN fabric 880 generally represents any type or form of computer network or architecture capable of facilitating communication between a plurality of storage devices. SAN fabric 880 may facilitate communication between servers 840 and 845 and a plurality of storage devices 890(1)-(N) and/or an intelligent storage array 895. SAN fabric 880 may also facilitate, via network 850 and servers 840 and 845, communication between client systems 810, 820, and 830 and storage devices 890(1)-(N) and/or intelligent storage array 895 in such a manner that devices 890(1)-(N) and array 895 appear as locally attached devices to client systems 810, 820, and 830. As with storage devices 860(1)-(N) and storage devices 870(1)-(N), storage devices 890(1)-(N) and intelligent storage array 895 generally represent any type or form of storage device or medium capable of storing data and/or other computer-readable instructions.

In certain embodiments, and with reference to example computing system 710 of FIG. 7, a communication interface, such as communication interface 722 in FIG. 7, may be used to provide connectivity between each client system 810, 820, and 830 and network 850. Client systems 810, 820, and 830 may be able to access information on server 840 or 845 using, for example, a web browser or other client software. Such software may allow client systems 810, 820, and 830 to access data hosted by server 840, server 845, storage devices 860(1)-(N), storage devices 870(1)-(N), storage devices 890(1)-(N), or intelligent storage array 895. Although FIG. 8 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 840, server 845, storage devices 860(1)-(N), storage devices 870(1)-(N), storage devices 890(1)-(N), intelligent storage array 895, or any combination thereof. All or a portion of one or more of the example embodiments disclosed herein may also be encoded as a computer program, stored in server 840, run by server 845, and distributed to client systems 810, 820, and 830 over network 850.

As detailed above, computing system 710 and/or one or more components of network architecture 800 may perform and/or be a means for performing, either alone or in combination with other elements, one or more steps of an example method for securing computing devices that are not in users' physical possessions.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

According to some examples, all or a portion of example system 100 in FIG. 1 may represent portions of, communicate with, and/or receive protection from one or more systems for endpoint security. As used herein, the term "endpoint security" may refer to the protection of endpoint systems from unauthorized and/or illegitimate use, access, and/or control. Examples of systems for endpoint protection may include, without limitation, anti-malware systems, user authentication systems, encryption systems, privacy systems, spam-filtering services, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

In addition, one or more of the modules described herein may transform data, physical devices, and/or representations of physical devices from one form to another. For example, one or more of the modules recited herein may receive biological measurements to be transformed, transform the biological measurements in to a determination that a computing device of a user is no longer in the user's possession, output a result of the transformation to a security system, use the result of the transformation to initiate a security action, and store the result of the transformation to a security log. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A computer-implemented method for securing computing devices that are not in users' physical possessions, at least a portion of the method being performed by a computing device of a user comprising at least one processor, the method comprising:
    configuring the computing device and an additional computing device of the user to exchange trusted heartbeat messages through the user's body;
    transmitting, from the additional computing device, a first heartbeat message through the user's body;
    receiving, at the computing device while the user is in physical possession of the computing device, the first heartbeat message through the user's body;
    transmitting, from the additional computing device after the first heartbeat message is transmitted, a second heartbeat message through the user's body;
    attempting, at the computing device, to receive the second heartbeat message through the user's body;
    failing, at the computing device, to receive the second heartbeat message through the user's body;
    determining, based at least in part on failing to receive the second heartbeat message through the user's body, that the user is no longer in physical possession of the computing device; and
    performing, at the computing device in response to determining that the user is no longer in physical possession of the computing device, a security action.

2. The computer-implemented method of claim 1, wherein performing the security action comprises locking the computing device.

3. The computer-implemented method of claim 1, further comprising:
taking, at the computing device while the user is in physical possession of the computing device, a first measurement of a biological attribute of the user's body;
taking, at the computing device, a second measurement of the same biological attribute; and
analyzing, at the computing device, the second measurement relative to the first measurement to determine that the user is no longer in physical possession of the computing device.

4. The computer-implemented method of claim 3, wherein:
a thief stole the computing device after the first measurement was taken;
the second measurement comprises a measurement of the same biological attribute of the thief's body; and
analyzing the second measurement relative to the first measurement to determine that the user is no longer in physical possession of the computing device comprises determining that a difference between the second measurement and the first measurement indicates that the first measurement and the second measurement were taken from different individuals.

5. The computer-implemented method of claim 3, wherein:
the second measurement comprises an attempted measurement of the biological attribute of the user's body; and
analyzing the second measurement relative to the first measurement to determine that the user is no longer in physical possession of the computing device comprises determining that a difference between the second measurement and the first measurement indicates that the second measurement was taken when the user was no longer in physical possession of the computing device.

6. The computer-implemented method of claim 3, wherein the biological attribute comprises an electric signal.

7. The computer-implemented method of claim 3, wherein the biological attribute comprises an electromagnetic field.

8. The computer-implemented method of claim 3, wherein the biological attribute comprises a biological heartbeat.

9. The computer-implemented method of claim 3, wherein the biological attribute comprises a hydration level.

10. The computer-implemented method of claim 3, wherein the biological attribute comprises a stress level.

11. The computer-implemented method of claim 3, wherein the biological attribute comprises an electrical impedance.

12. The computer-implemented method of claim 3, wherein the biological attribute comprises a skin tone.

13. The computer-implemented method of claim 3, wherein the biological attribute comprises a skin thickness.

14. A system for securing computing devices that are not in users' physical possessions, the system comprising:
a configuring module, stored in memory of a computing device of the user, that configures the computing device and an additional computing device of the user to exchange trusted heartbeat messages through the user's body;
a transmitting module, stored in the additional computing device's memory, that:
transmits, from the additional computing device, a first heartbeat message through the user's body; and
transmits, from the additional computing device after the first heartbeat message is transmitted, a second heartbeat message through the user's body,
a measuring module, stored in the computing device's memory, that:
receives the first heartbeat message through the user's body
attempts to receive the second heartbeat message through the user's body; and
fails to receive the second heartbeat message through the user's body;
an analyzing module, stored in the computing device's memory, that determines, based at least in part on the second heartbeat message failing to be receive through the user's body, that the user is no longer in physical possession of the computing device;
a security module, stored in the computing device's memory, that performs, at the computing device in response to determining that the user is no longer in physical possession of the computing device, a security action; and
at least one physical processor that executes the measuring module, the analyzing module, and the security module.

15. The system of claim 14, wherein
the security module performs the security action by locking the computing device.

16. The system of claim 14, wherein:
the measuring module further:
takes, at the computing device while the user is in physical possession of the computing device, a first measurement of a biological attribute of the user's body; and
takes, at the computing device, a second measurement of the same biological attribute; and
the analyzing module further analyzes, at the computing device, the second measurement relative to the first measurement to determine that the user is no longer in physical possession of the computing device.

17. The system of claim 16, wherein:
a thief stole the computing device after the first measurement was taken;
the second measurement comprises a measurement of the same biological attribute of the thief's body; and
the analyzing module analyzes the second measurement relative to the first measurement to determine that the user is no longer in physical possession of the computing device by determining that a difference between the second measurement and the first measurement indicates that the first measurement and the second measurement were taken from different individuals.

18. The system of claim 16, wherein:
the second measurement comprises an attempted measurement of the biological attribute of the user's body; and
the analyzing module analyzes the second measurement relative to the first measurement to determine that the user is no longer in physical possession of the computing device by determining that a difference between the second measurement and the first measurement indicates that the second measurement was taken when the user was no longer in physical possession of the computing device.

19. The system of claim 16, wherein the biological attribute comprises at least one of:

an electric signal;
an electromagnetic field;
a biological heartbeat;
a hydration level;
a stress level;
an electrical impedance;
a skin tone; and
a skin thickness.

20. A non-transitory computer-readable medium comprising one or more computer-executable instructions that, when executed by at least one processor of a computing device of a user, cause the computing device to:
   configure the computing device of the user to exchange trusted heartbeat messages with an additional computing device of the user through the user's body;
   receive, at the computing device while the user is in physical possession of the computing device, a first heartbeat message transmitted from the additional computing device through the user's body;
   attempt, at the computing device, to receive a second heartbeat message transmitted from the additional computing device through the user's body;
   fail, at the computing device, to receive the second heartbeat message through the user's body;
   determine, based at least in part on failing to receive the second heartbeat message through the user's body, that the user is no longer in physical possession of the computing device; and
   perform, at the computing device in response to determining that the user is no longer in physical possession of the computing device, a security action.

* * * * *